| United States Patent [19] | [11] Patent Number: 4,841,070 |
|---|---|
| Pauling et al. | [45] Date of Patent: Jun. 20, 1989 |

[54] SULFINYL-ASCORBIC ACID USEFUL AS AN ANTI-OXIDANT

[75] Inventors: Horst Pauling, Bottmingen; Christof Wehrli, Witterswil, both of Switzerland

[73] Assignee: Hoffmann-La Roche Inc., Nutley, N.J.

[21] Appl. No.: 211,514

[22] Filed: Jun. 24, 1988

[30] Foreign Application Priority Data

Jul. 9, 1987 [CH] Switzerland ................. 2616/87
Apr. 25, 1988 [CH] Switzerland ................. 1536/88

[51] Int. Cl.$^4$ ............................................. C07D 411/04
[52] U.S. Cl. ............................................. 549/34
[58] Field of Search ................................. 549/34

[56] References Cited

FOREIGN PATENT DOCUMENTS 0146121 6/1985 European Pat. Off. .
1217970 6/1966 Fed. Rep. of Germany ........ 549/34
61-236772 1/1986 Japan .
61-227578 9/1986 Japan .
1227578 10/1986 Japan ......................... 549/34

OTHER PUBLICATIONS

Murakami, Chem. Abst., vol. 74, No. 17, pp. 465–466, 88266c (Apr. 1971).
Wang, 92, Chem. Abst., No. 19, p. 627, 92:164180j (1979).
Timoschchuk, Chem. Abst., 102, p. 751, 102:113861z (1985).

*Primary Examiner*—Mary C. Lee
*Assistant Examiner*—E. Brendan Magrab
*Attorney, Agent, or Firm*—Jon S. Saxe; George M. Gould; William H. Epstein

[57] ABSTRACT

The novel 5,6-sulfinyl-L-ascorbic acid and its stereoisomers, their manufacture by sulfinylating L-ascorbic acid or corresponding stereoisomers, compositions having oxidation-inhibiting properties which contain 5,6-sulfinyl-L-ascorbic acid or a stereoisomer thereof as well as the use of 5,6-sulfinyl-L-ascorbic acid or a stereoisomer thereof as an antioxidant are described.

5 Claims, No Drawings

SULFINYL-ASCORBIC ACID USEFUL AS AN ANTI-OXIDANT

SUMMARY OF THE INVENTION

The invention is concerned with novel antioxidants, namely 5, 6-sulfinyl-L-ascorbic acid, i.e. the compound of the formula

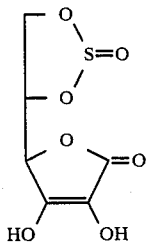

I and its stereoisomers, i.e. the compounds of the formulae

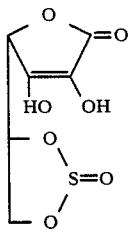

II (5,6-sulfinyl-D-ascorbic acid)

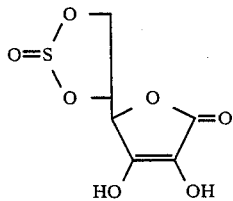

III (5,6-sulfinyl-D-erythorbic acid) and

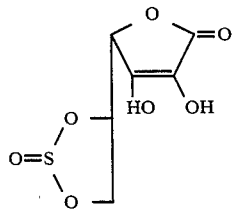

IV (5,6-sulfinyl-L-erythorbic acid)

The invention is also concerned with a process for the manufacture of 5,6-sulfinyl-L-ascorbic acid and its stereoisomers. This process comprises sulfinylating L-ascorbic acid or any of its stereoisomers, i.e. D-ascorbic acid, D-erythorbic acid or L-erythorbic acid.

Finally, the invention is concerned with the use of the compounds I to IV as antioxidants or stabilizers as well as compositions having oxidation-inhibiting properties, which contain 5,6-sulfinyl-L-ascorbic acid or a stereoisomer thereof.

DETAILED DESCRIPTION

The compounds I through IV have been found to provide anti-oxidant properties to substrates for protecting these substrates against deterioration due to oxidation. In accordance with this invention any substrate subject to oxidative deterioration can be prevented from such deterioration by incorporating as an anti-oxidant an effective amount of any one of 5,6-sulfinyl-L-ascorbic acid or its stereoisomers.

The stereoisomers of 5,6-sulfinyl-L-ascorbic acid include both its enantiomers as well as its diastereoisomers. The particular compounds of formulae I to IV are formed from the sulfination of L-ascorbic acid or its stereoisomers.

The sulfinylation of L-ascorbic acid or of its stereoisomers is conveniently effected by using thionyl chloride as the sulfinylating agent. The reaction partners are conveniently reacted in approximately equimolar amounts, preferably in as close as possible equimolar amounts. Moreover, the sulfinylation is conveniently effected at temperatures of about −20° C. to about 50° C. A preferred range is that of about −10° C. to about 25° C.

The sulfinylation is conveniently carried out in the presence of an inert solvent, especially a polar aprotic solvent; examples of such solvents are: acyclic di- and polyethers such as monoglyme (1,2-dimethoxyethane) and diethylene glycol dimethyl ether; cyclic mono- and diethers such as tetrahydrofuran and dioxan; sulfolane (tetrahydrothiophene 1,1-dioxide); dimethylformamide; dimethylacetamide; N-methylpyrrolidone; and acetonitrile.

The novel compounds exhibit interesting oxidation-inhibiting properties and can be used in any conventional substrate subject to oxidative deterioration. Among these substrates are included the use of the compounds of formulas I to IV:

in foodstuffs [wine (especially for its sulphurization), vinegar, edible oils and fats, beer, fruit and vegetable juices, syrups, meat and sausage products, dried fruit, dried vegetables, nuts, fruit and vegetable preserves, potato products, spreads, sauces, mayonnaise, etd]

in feedstuffs such as animal feedstuffs in boiler feed water in materials for the manufacture and development of film in printing materials in materials for the manufacture and treatment of textiles in plastics in lubricating oils and greases in rubber The amount of the compound I, II, III or IV which is conveniently used can be any amount which will be effective in retarding oxidation. If desired, this amount can be small. The preferred amount corresponds approximately to the amount of other antioxidants of the sulfite type which is used, thus e.g. it conveniently amounts to about 1 to 7000 parts by weight of this compound per million parts by weight of substrate and compound, especially from about 20 to about 2000 ppm. The preferred amount depends on the purpose of use. In the foodstuff industry this preferred amount is, for example:

for wine: about 50–300 ppm for dried fruit: about 1000–7000 ppm for fruit and vegetable juices: about 80–300 ppm.

In all these examples, ppm refers to parts by weight of the compound of formula I, II, III or IV per million parts by weight of the substrate and compound I, II, III or IV.

The novel compounds I to IV can be added as such to the substrate to be protected or, where appropriate, also in diluted form, e.g. as a solution, especially as an aqueous or alcoholic solution.

In the case of higher concentrations ($\geq 2$ mg/ml substrate) the compounds I to IV have, moreover, a bacteriological and fungicidal effect.

EXAMPLE 17.6 g (100 mmol) of crystalline L-ascorbic acid and 50 ml of tetrahydrofuran are placed under a protective gas atmosphere ($N_2$) in a 350 ml four-necked sulfonation flask equipped with a thermometer and a stirrer. Thereto there are added at 0° C. 7.42 ml (102 mmol) of thionyl chloride and the mixture is stirred at 0° C. for 24 hours. After this time the ascorbic acid has dissolved almost completely. The solution is poured on to 200 g of ice/water and extracted in 4 separating funnels with $4 \times 200$ ml of ethyl acetate. The organic phases are washed with $8 \times 50$ ml of 20% sodium chloride solution. The ethyl acetate phases are combined, dried over sodium sulphate and concentrated to dryness on a rotary evaporator in a water-jet vacuum. The residue (21.2 g) is dissolved in 45 ml of ethyl acetate. A small amount of insoluble constituent is filtered off under suction and rinsed with 5 ml of ethyl acetate. 100 ml of toluene are slowly added dropwise to the filtrate while stirring. After seeding the mixture is stirred for 18 hours. The product is filtered off under suction and dried to constant weight for 8 hours at 45° C. in a water-jet vacuum. There are obtained 17.6 g of 5,6-sulfinyl-L-ascorbic acid (79% of the theoretical yield); melting point 150°–151° C. (decomposition); $[\alpha]20/365 = +246.2°$(1% in $H_2O$).

| | Elemental analysis: | | |
| --- | --- | --- | --- |
| | C % | H % | S % |
| Calc. | 32.44 | 2.72 | 14.43 |
| Found | 32.68 | 2.66 | 14.00 |

The synthesis of the corresponding 5,6-sulfinylated derivative proceeds analogously using D-ascorbic acid, D-erythorbic acid or L-erythorbic acid.

We claim:

1. A compound selected from the group consisting of 5,6-sulfinyl-L-ascorbic acid and its stereoisomers.

2. The compound of claim 1 wherein said compound is 5,6-sulfinyl-L-ascorbic acid.

3. The compound of claim 1 wherein said compound is 5,6-sulfinyl-D-ascorbic acid.

4. The compound of claim 1 wherein said compound is 5,6-sulfinyl-D-erythorbic acid.

5. The compound of claim 1 wherein said compound is 5,6-sulfinyl-L-erythorbic acid.

* * * * *